US012685638B2

(12) United States Patent
Wolf

(10) Patent No.: US 12,685,638 B2
(45) Date of Patent: Jul. 21, 2026

(54) PENILE PROSTHESIS PUMP HAVING A DEFLATE VALVE ASSEMBLY INCLUDING A GROOVED VALVE STEM DISPOSED IN A SLEEVE

(71) Applicant: Coloplast A/S, Humlebaek (DK)

(72) Inventor: Donald Wolf, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 1170 days.

(21) Appl. No.: 17/690,011

(22) Filed: Mar. 9, 2022

(65) Prior Publication Data

US 2023/0285150 A1 Sep. 14, 2023

(51) Int. Cl.
*A61F 2/26* (2006.01)

(52) U.S. Cl.
CPC ........ *A61F 2/26* (2013.01); *A61F 2250/0078* (2013.01)

(58) Field of Classification Search
CPC ............................ A61F 2/26; A61F 2250/0078
See application file for complete search history.

(56) References Cited

U.S. PATENT DOCUMENTS

| | | | |
|---|---|---|---|
| 4,224,934 A | 9/1980 | Scott et al. | |
| 4,383,525 A | * 5/1983 | Scott | A61F 2/26 |
| | | | 600/40 |
| 4,453,411 A | 6/1984 | Shikasho | |
| 4,566,446 A | 1/1986 | Fogarty | |

| | | | |
|---|---|---|---|
| 4,576,234 A | 3/1986 | Upchurch | |
| 5,141,509 A | 8/1992 | Burton et al. | |
| 5,254,092 A | 10/1993 | Polyak | |
| 5,823,991 A | 10/1998 | Shim | |
| 6,171,233 B1 | 1/2001 | Willard | |
| 6,929,599 B2 | 8/2005 | Westrum, Jr. | |
| 7,244,227 B2 | 7/2007 | Morningstar | |
| 7,250,026 B2 | 7/2007 | Kuyava | |
| 7,350,538 B2 | 4/2008 | Kuyava et al. | |
| 7,438,682 B2 | 10/2008 | Henkel et al. | |
| 7,637,861 B2 | 12/2009 | Kuyava et al. | |
| 7,874,978 B2 | 1/2011 | Kuyava et al. | |
| 7,914,439 B2 | 3/2011 | Kuyava et al. | |
| 8,062,209 B2 | 11/2011 | Rowland et al. | |
| 8,109,870 B2 | 2/2012 | Kuyava et al. | |
| 8,167,788 B2 | 5/2012 | Fogarty et al. | |
| 8,337,392 B2 | 12/2012 | Morningstar | |
| 8,939,889 B1 | 1/2015 | Chechik | |

(Continued)

FOREIGN PATENT DOCUMENTS

| | | |
|---|---|---|
| CA | 2824259 A1 | 3/2014 |
| EP | 2957263 A1 | 12/2015 |

(Continued)

*Primary Examiner* — Charles A Marmor, II
(74) *Attorney, Agent, or Firm* — Coloplast Corp., Coloplast A/S; Nick Baumann

(57) ABSTRACT

A pump for an implantable penile prosthesis has a pump body attachable between a penile implant and a reservoir containing a liquid. A deflate valve assembly is placed within the pump body and has a sleeve sealed inside of the pump body and a stem that is movable longitudinally within the sleeve. A groove is formed in an exterior surface of the stem. The stem is longitudinally movable within the sleeve to align the groove with both an inlet flow path and an exhaust flow path to form a deflation flow path between the penile implant and the reservoir.

17 Claims, 12 Drawing Sheets

(56) References Cited

U.S. PATENT DOCUMENTS

| | | | |
|---|---|---|---|
| 9,987,136 B2 | 6/2018 | Daniel | |
| 2002/0082471 A1* | 6/2002 | Henkel | A61F 2/26 |
| | | | 600/39 |
| 2002/0082472 A1 | 6/2002 | Derus et al. | |
| 2002/0082473 A1 | 6/2002 | Henkel et al. | |
| 2002/0082709 A1 | 6/2002 | Almli et al. | |
| 2004/0220447 A1 | 11/2004 | Morningstar | |
| 2005/0137578 A1 | 6/2005 | Heruth et al. | |
| 2005/0250981 A1 | 11/2005 | Kuyava et al. | |
| 2006/0135845 A1 | 6/2006 | Kuyava et al. | |
| 2007/0142700 A1 | 6/2007 | Fogarty et al. | |
| 2007/0276342 A1 | 11/2007 | Lin et al. | |
| 2011/0118540 A1 | 5/2011 | Morningstar | |
| 2011/0201880 A1 | 8/2011 | Fogarty | |
| 2013/0072751 A1 | 3/2013 | Fogarty | |
| 2016/0100946 A1* | 4/2016 | Fogarty | A61F 5/41 |
| | | | 600/40 |
| 2018/0042724 A1 | 2/2018 | DiLoreto | |

FOREIGN PATENT DOCUMENTS

| | | | |
|---|---|---|---|
| EP | 2965719 A1 | 1/2016 | |
| WO | 98/04214 A1 | 2/1998 | |
| WO | 01/47441 A2 | 7/2001 | |
| WO | 2006/066199 A1 | 6/2006 | |
| WO | 2007/073556 A2 | 6/2007 | |
| WO | 2012/139589 A1 | 10/2012 | |
| WO | 2015/093681 A1 | 6/2015 | |

* cited by examiner

DEFLATION MODE

INFLATION MODE

DEFLATION MODE

PENILE PROSTHESIS PUMP HAVING A DEFLATE VALVE ASSEMBLY INCLUDING A GROOVED VALVE STEM DISPOSED IN A SLEEVE

BACKGROUND

An implanted penile prosthetic is a proven approach to relieve erectile dysfunction for male users.

An inflatable penile prosthesis typically includes one or more cylinders that are implantable in the corpora cavernosa of the penis, a reservoir implantable in the abdomen that communicates with the cylinder(s), and a pump, often located in the scrotum, that is employed to move liquid from the reservoir into the cylinder(s).

Typically, in an inflation mode of the inflatable penile prosthetic, the user squeezes a bulb of the pump multiple times to draw liquid out of the reservoir and push the liquid to the cylinders implanted in the penis. After the first squeeze of the pump bulb, recovery of the bulb forms a suction that draws liquid into the bulb from the reservoir, and each squeeze thereafter transfers liquid from the bulb into the cylinders implanted in the penis. Squeezing of the bulb in the inflation mode of the pump inflates the implant to provide the user with an erect penis. The user may return the penis to its flaccid state by selectively transferring the liquid from the implant back into the reservoir through a deflation mode of the pump.

FIG. 1 shows a prior art pump body 20 in a deflation mode with a liquid path flowing from the previously inflated cylinders implanted in the penis back to the reservoir.

The pump body 20 portion of a pump is shown and is connected between a reservoir 22 and an implant 24. A movable valve 26 is sealed inside of the pump body 20 and is biased by a spring 28. In the deflation mode as shown, the valve 26 has been pushed in a downward direction (relative to FIG. 1) with a portion of the valve 26 held within, or secured, in a valve seat 30. The valve seat 30 is, in this example, an annular ring of material formed by a channel 32 inside the pump body 20. A part of the valve 26 is larger than the annular ring, or valve seat 30, so that the valve 26 is retained in its valve seat 30 until displaced.

As noted above for the inflation mode, squeezing the pump bulb draws liquid out from the reservoir 22 and moves the liquid through the pump body 20 and into the implant 24. Each subsequent squeeze of the pump bulb removes more volume from the reservoir 22 and displaces that volume into the implant 24. Depending on the strength of the user's hand and the size of the pump bulb, it can take about 30 squeezes or more to inflate the implant 24 to a desired hardness.

In the deflation mode shown in FIG. 1, the user has pressed on a deflation pad 34 to move the valve 26 downward to a deflation position, during which time the liquid in the implant 24 follows a deflation path D from the implant 24, through the pump body 20, and back to the reservoir 22. The implant 24 is thus flaccid, or mostly empty of liquid.

Consequently, the next time the user desires to inflate the implant 24 the valve 26 will be in the down position, or the deflation position, and secured in its valve seat 30 of the annular ring. If the liquid from the reservoir 22 is moved with a sufficient force (provided by the user's hand), then the valve 26 is displaced upward out of engagement with the valve seat 30 of the annual ring and into its inflation position to open the pathway under the valve 26 for liquid to flow toward the implant 24. It follows that displacing the valve 26 from the deflation position to the inflation position necessitates displacing the valve 26 from its valve seat 30 with a force that is sufficient to overcome the engagement between the valve 26 and its seat 30 (the annular ring engaged around the valve 26). The annular ring 30 has a diameter that is smaller than the valve 26, which is to say that the valve seat 30 is narrower than the valve 26 so the valve 26 is captured in the narrower valve seat 30. The force needed to move the valve 26 out of engagement with the valve seat 30 is called the "crack force." If one listens closely when operating the prior art pump in FIG. 1, the movement of the valve 26 out of engagement with the valve seat 30 can be heard as a "pop," and this is one reason for the term "crack force." Some users, particularly users with limited dexterity, have difficulty in squeezing the pump bulb with enough force to overcome the crack force and move the valve 26 off the valve seat 30. These users will have the impression that some feature of the pump is not working correctly. In fact, the pump works as designed but such a user has insufficient hand strength to overcome the crack force of the valve 26 in its seat 30.

Surgeons and user would benefit from an improved pump that reduces or eliminates the crack force problem discussed above that is associated with the prior art pump body 20 shown in FIG. 1.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
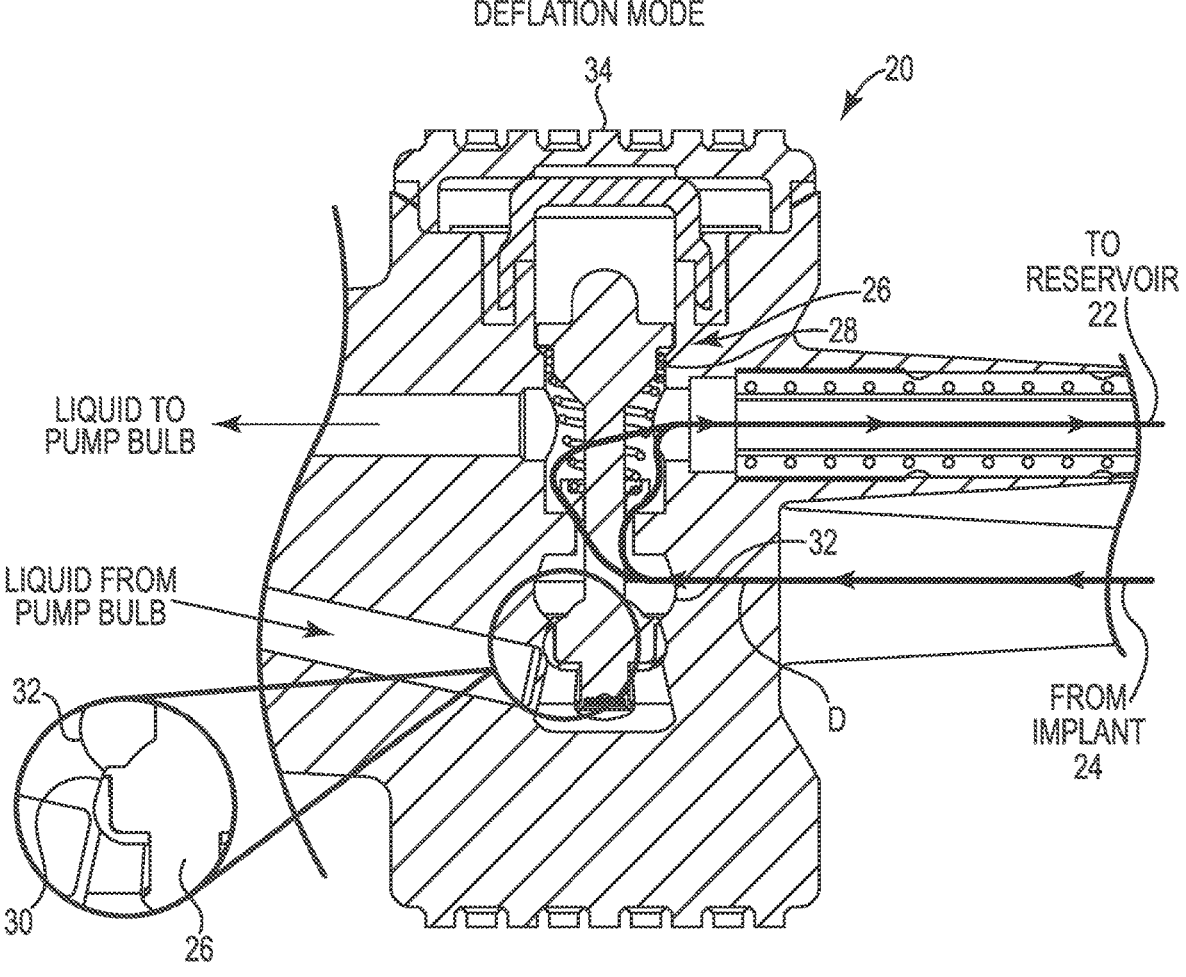
FIG. 1 is a cross-sectional view of a prior art pump body in a deflation mode showing a valve engaged in a valve seat.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense.

It is to be understood that the features of the various exemplary embodiments described herein may be combined with each other, unless specifically noted otherwise.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described.

Embodiments provide a pump adapted to inflate an implantable penile prosthesis, the pump comprising: a pump body adapted to be coupled between a penile implant and a reservoir containing a liquid; an inlet flow path formed in the pump body that is configured to allow the liquid to enter the pump body from the reservoir; an exhaust flow path formed in the pump body that is configured to allow the liquid to exit the pump body and flow to the penile implant; and a deflate valve assembly comprising a sleeve sealed inside of the pump body and a stem that is movable longitudinally within the sleeve, with a groove formed in an exterior surface of the stem. The stem is longitudinally movable within the sleeve to align the groove with both the inlet flow path and the exhaust flow path to form a deflation flow path between the penile implant and the reservoir. The benefit of the groove that is movable into alignment with both the inlet and exhaust flow paths is that displacement of the stem (and its groove) can be accomplished without having to overcome the crack force associated with moving the stem out of engagement with a narrower valve seat, and thus the crack force, or the force to overcome the seal of the stem in the pump is zero. The disclosed valve assembly has a groove that is movable into alignment with both the inlet and exhaust flow paths and solves the problem of a crack force that can be difficult for some people to overcome, given their limited hand strength.

Aspects of the embodiments include forming the pump body and the sleeve to include an inlet lumen formed through the sleeve and an exhaust lumen formed through the sleeve and separate from the inlet lumen, with the inlet lumen aligned with the inlet flow path and the exhaust lumen aligned with the exhaust flow path. The advantage of this arrangement is to mate the groove in the stem with the flow paths when the valve assembly is in the deflation mode.

Aspects of the embodiments include having a base of the stem is biased relative to a base of the sleeve by a spring. The advantage of the spring is to automatically return the valve assembly back to the inflation mode after the liquid is emptied or deflated from the implants. Alternatively, the stem of the valve could be manually pushed back to the inflation mode.

Aspects of the embodiments include providing a pump bulb coupled to the pump body, where the pump bulb is operable to draw the liquid out of the reservoir and eject the liquid to the penile implant. The advantage of a pump bulb is to provide pressure generation or a liquid motive force or a suction force. Other pressure generators are acceptable.

Aspects of the embodiments include inserting the stem into the sleeve so the stem is non-concentric relative to the sleeve. The advantage to this orientation is to ensure that the generally round (or cylindrical) stem does not rotate within the sleeve during use.

Aspects of the embodiments include providing the stem with a base portion and a cylindrical portion, with a distal end of the cylindrical portion of the stem connected to the base portion and a rounded proximal end of the cylindrical portion of the stem movable through a proximal end of the sleeve. Having a portion of the stem project out of the sleeve allows access for a user to move the stem through the pump body, and thus access to displace the stem within the sleeve.

Aspects of the embodiments include providing the base portion of the stem with a planar distal face, a wall orthogonal to and extending from the planar distal face, and a chamfered surface extending between the wall and the cylindrical portion of the stem. The distal face provides and engagement surface for a spring and the chamfered surface provides a large sealing surface for the stem relative to the channel.

Aspects of the embodiments include providing the base portion with a base width that is larger than a width of the cylindrical portion of the stem. The wider base ensures that the stem remains within the channel of the pump body and also provides a larger sealing surface for the stem relative to the sleeve.

Aspects of the embodiments include providing the pump body with a compliant touch pad located on an exterior surface of the pump body, and the compliant touch pad is movable to contact a proximal end of the stem and longitudinally move the stem within the sleeve. The advantage of a compliant touch pad is to allow all users, even users with limited hand strength, to displace the stem within the sleeve.

Aspects of the embodiments include providing the groove with a longitudinal segment aligned with a longitudinal axis of the stem and a lateral segment connected to and extending from the longitudinal segment. The lateral segment of the groove allows the deflation flow path to be offset or on a different axis than the inlet flow path.

Aspects of the embodiments include providing the lateral segment of the groove at a 90 degree angle relative to the longitudinal segment to allow the inlet path to be offset by 90 degrees from the exhaust flow path. This provides the pump designer with layout options.

Aspects of the embodiments include providing the groove with a curved segment connected between the longitudinal segment and the lateral segment. This allows molding or machining the groove into the stem to allow for a smooth deflation flow path with low resistance to quickly deflate the implants.

Aspects of the embodiments include spacing the inlet flow path a first distance away from the exhaust flow path, and a distal end of the longitudinal segment of the groove is spaced apart from the lateral segment by the first distance. This spacing ensures that the groove will span the two flow paths for efficient deflation of the implants.

Aspects of the embodiments include a semicircular groove when viewed in a cross-section orthogonal to a longitudinal axis of the stem. The advantage is that this style of groove may be formed accurately and efficiently with a ball-end mill.

Aspects of the embodiments include a rectangular stem with a base portion and a rectangular projection extending from the base portion and the groove includes a longitudinal segment formed in a first face of the rectangular projection of the stem and a lateral segment formed in a second adjacent face of the rectangular projection of the stem. A rectangular stem will not rotate within its (rectangular) sleeve.

Aspects of the embodiments include a triangular stem with a base portion and a triangular projection extending from the base portion and the groove includes a longitudinal segment formed in a first face of the triangular projection of the stem and a lateral segment formed along a portion of the first face of the triangular projection of the stem and along a portion of a second adjacent face of the triangular projection of the stem. The triangular stem is compact and will not rotate within its (triangular) sleeve.

Aspects of the embodiments include inserting the cylindrical portion of the stem into a cylindrical recess formed in the sleeve such that an initial movement of the cylindrical portion of the stem within the cylindrical recess in the sleeve is characterized by an absence of a crack force.

Figure 2:
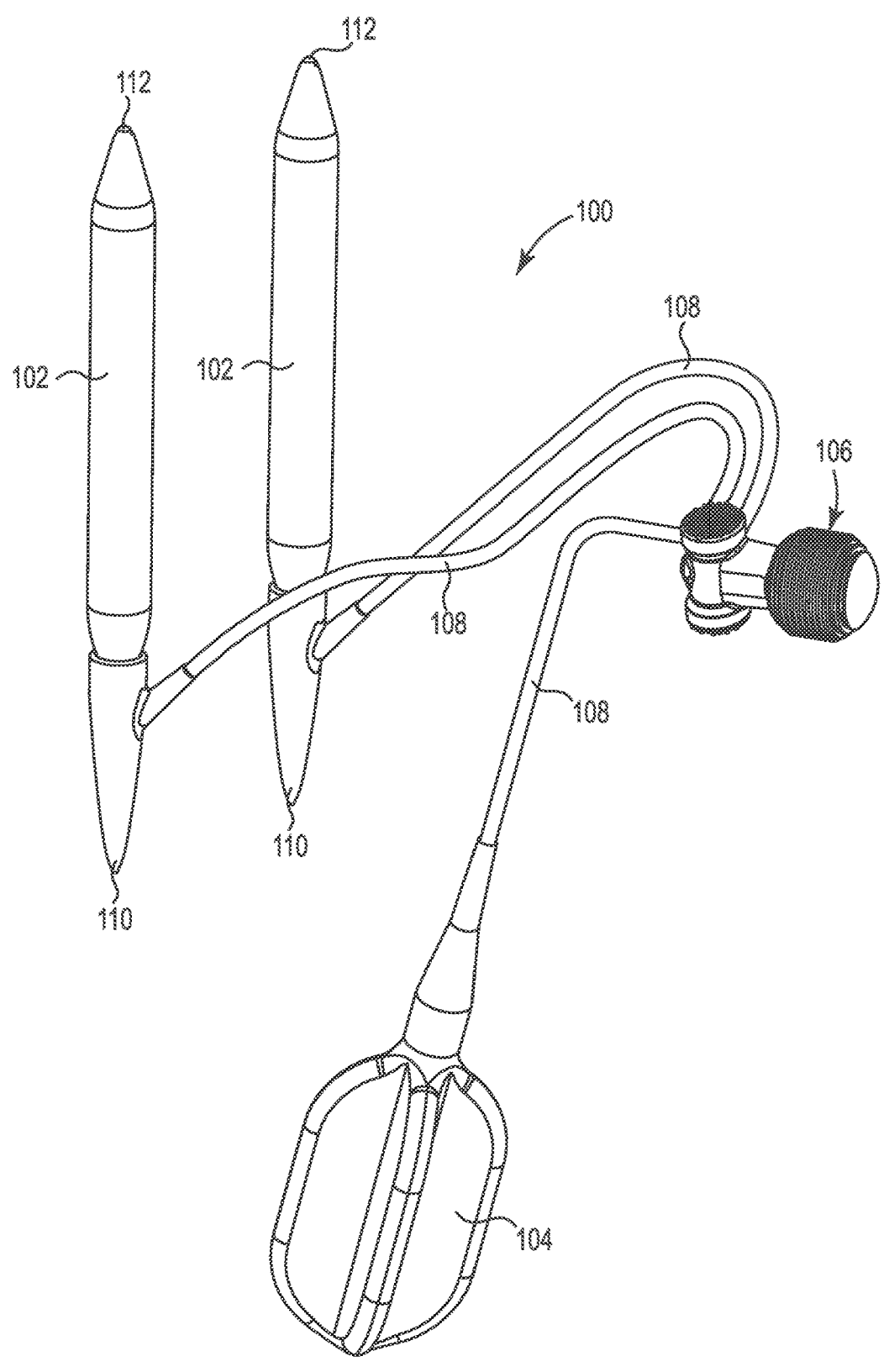
FIG. 2 is a perspective view of one embodiment of an inflatable penile prosthesis including a pump, a reservoir, and a pair of implants implantable into the penis.

FIG. 2 is a perspective view of an inflatable penile prosthesis 100 according to one embodiment. The inflatable penile prosthesis 100 includes a pair of inflatable cylinders 102 for implantation into a penis (the implants), a reservoir 104, and a pump 106. The surgeon implants the components and attaches the components together by connecting the cylinders 102 and the reservoir 104 to the pump 106, for example with kink resistant or other suitable tubing 108. The inflatable penile prosthesis 100 can be provided in a kit of parts including tubing clamps, connector tools, pinching tools, and the like that allows a surgeon to connect the components as s/he implants the prosthesis 100.

Each of the inflatable cylinders 102 (also called an inflatable penile implant 102 since each cylinder 102 is implantable in the penis) includes a proximal end 110 opposite a distal end 112. During implantation, the proximal end 110 (also called a rear tip) is implanted toward the crus of the penis and the distal end 112 is implanted within the glans penis. The cylinders 102 are fabricated from material configured to collapse when the cylinders 102 are deflated to provide the penis with a flaccid state and expand (like a balloon) when the cylinders 102 are inflated with liquid to provide the penis with an erection. As a point of reference, the cylinders 102 of FIG. 2 are illustrated in an inflated state. Suitable material for fabricating the cylinders 102 includes silicone, biocompatible polymers such as urethanes, blends of polymers with urethane, copolymers of urethane, or the like. Suitable cylinders are available from Coloplast Corp., Minneapolis, Minnesota.

The reservoir 104 is sized to maintain a volume of liquid between about 50-300 ml. In one embodiment, the reservoir 104 is provided as a "cloverleaf" style of reservoir having multiple leaves that may be folded one against the other to compact the reservoir 104 for implantation into the abdomen of the user. One suitable reservoir 104 is sized to retain approximately 130 mL of liquid and is available from Coloplast Corp., Minneapolis, Minnesota.

Figure 3:
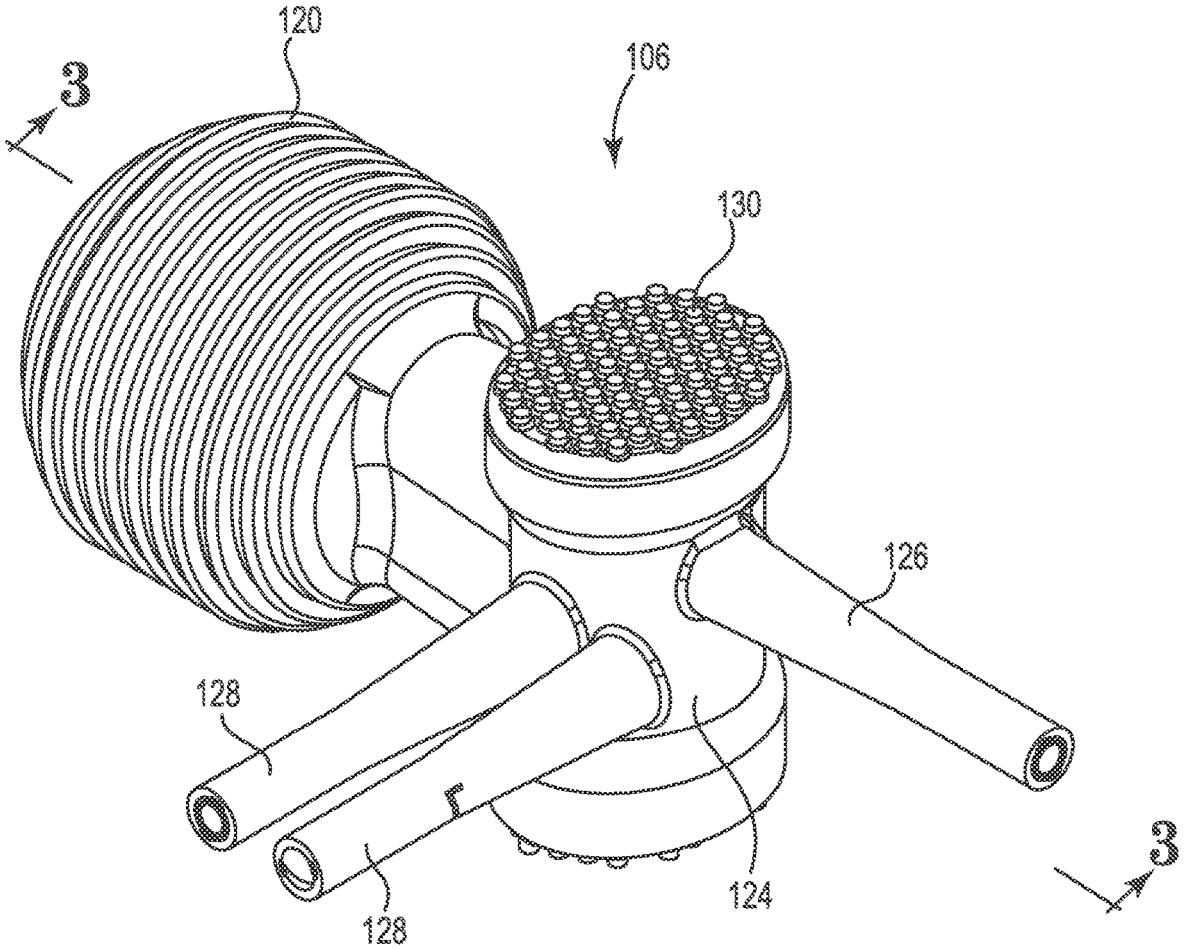
FIG. 3 is a perspective view of the pump illustrated in FIG. 2.

FIG. 3 is a perspective view of the pump 106. The pump 106 includes a pump bulb 120 integrated with a pump body 124, an inlet tube 126 connected with the pump body 124, and a pair of exhaust tubes 128 extending from the pump body 124. The pump body 124 is adapted to be coupled between the cylinders 102 or the penile implants 102 (FIG. 2) and the reservoir 104 by suitable tubing that is attachable to the inlet tube 126 and the pair of exhaust tubes 128. The inlet tube 126 provides a pathway for liquid to flow from the reservoir 104 into the pump 106. Each of the exhaust tubes 128 extends from the pump 106 and is connected to one of the pair of the inflatable cylinders 102. Thus, there is one inlet tube 126 and two exhaust tubes 128 coupled with the pump 106.

We note here that the inlet tube 126 is located on right side a face of the pump body 124 and the two exhaust tubes 128 are located on a face oriented 90 degrees from the right side face. It is acceptable to locate the inlet tube 126 and the two exhaust tubes 128 on the same face if the designed chooses to fabricate a pump having a similar format as the prior art pump shown in FIG. 1. We have elected to offset the inlet tube 126 on a different face from the two exhaust tubes 128 to better show the flow paths into and out of the pump body 124. Other orientations are acceptable.

In one embodiment, the pump bulb 120 is flexible polymer and includes a ribbed structure that allows the pump bulb 120 to be grasped through the scrotum. The pump bulb 120 is coupled to the pump body 124 and is operable to draw the liquid out of the reservoir 104 and eject the liquid into the penile implant 102. During inflation of the implants 102, the pump bulb 120, when squeezed, collapses to drive liquid out of the pump bulb 120, through the pump body 124 out of the exhaust tubes 128, and to the implants 102. The bulb 120 is configured to recover after squeezing, which expands a size of the bulb 120 and creates a negative local pressure in the bulb 120 that draws additional liquid out of the reservoir 104 (FIG. 2), through the inlet tube 126 and the pump body 124, and into the pump bulb 120. The pump bulb 120 is thus readied for subsequent squeezing to drive liquid from the pump bulb 120 into the implants 102.

In one embodiment, the pump body 124 is integrally formed and connected with the pump bulb 120 and includes a deflation surface 130. The deflation surface 130 is illustrated as non-circular (elliptical) although other shapes for the deflation surface 130 are acceptable. The pump body 124 houses or maintains valves, including a deflate valve assembly (described below). During deflation of the implants 102, a user pressing on the deflation surface 130 deforms or flexes the surface 130, which displaces a stem of the deflate valve assembly to move the deflate valve from the inflation mode to the deflation mode. Since the implants 102 (FIG. 2) are pressurized when inflated, a movement of the stem of the deflate valve assembly to the deflation mode allows liquid in the inflated implants 102 to flow under pressure back to the reservoir 104 while bypassing the pump bulb 120. This allows swift deflation of the implants 102 with one press of the deflation surface 130.

Generally, the pump 106 is implanted into the scrotum of the user, the implants/cylinders 102 are implanted into the penis of the user, and the reservoir 104 is implanted within the abdomen of the user. The pump bulb 120 and the deflation surface 130 are accessed by the fingers of the user as he grasps the scrotum. A surgeon suitably couples the components together either during implantation or after placement of the components in the body. The pump 106 and the pump body 124 are fabricated from material suitable for body implantation, such as silicone or the urethane-based materials described above for the cylinders 102 or the reservoir 104.

Figure 4:
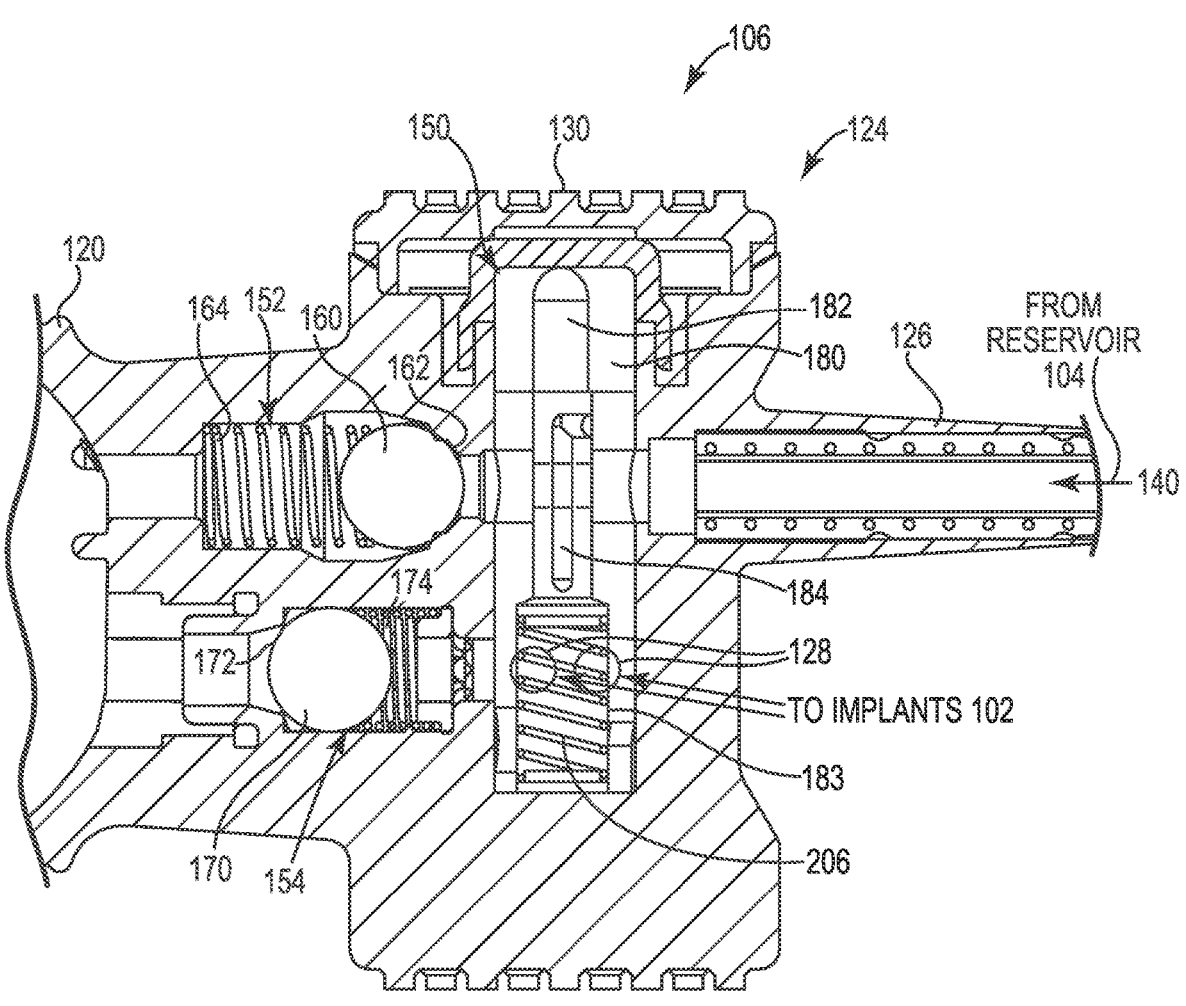
FIG. 4 is a partial cross-sectional view of a pump body housing one embodiment of a deflate valve assembly.

FIG. 4 is a partial cross-sectional view of the pump 106 showing the deflate valve assembly 150 contained within the pump body 124. The pump body 124 includes an inlet flow path 140 formed in the inlet tube 126 and an exhaust flow path (See FIG. 5 and labeled "TO IMPLANTS 102" in FIG. 4) that communicates with each of the exhaust tubes 128 (See FIG. 3). An inlet valve 152 is located in the inlet flow path 140 and communicates between the reservoir 104 and the pump bulb 120. And an exhaust valve 154 is located in the exhaust flow path 142 (See FIG. 5) and communicates between the pump bulb 120 and the cylinders 102. The deflate valve assembly 150 is located inside of the pump body 124 and is movable between (1) an inflation position that allows the liquid to flow along the inlet flow path and the exhaust flow path and (2) a deflation position that directs liquid flow from the implants 102 directly back to the reservoir 104 through a stem of the deflate valve assembly 150.

The deflate valve assembly 150 is described below and includes a sleeve 180 sealed inside of the pump body 124, a stem 182 that is movable longitudinally within a channel 183 formed in the sleeve 180, a groove 184 formed in an exterior surface 186 of the stem 182, and a spring 206 that biases the stem 182 within the channel 183 of the sleeve 180. The view of FIG. 4 shows two outlets (labeled "TO IMPLANTS 102") that are formed through the sleeve 180 to communicate with the exhaust tubes 128 (FIG. 3) that are integrated with the pump body 124.

The inlet valve 152 is a one-way valve placed in the pump body 124 to allow liquid to flow from the inlet flow path and into the pump bulb 120 and to prevent the flow of liquid from the pump bulb 120 back to the reservoir 104 during the pumping sequence. The inlet flow valve 152 includes a ball 160 that is biased into contact with a surface 162 by a spring 164. The ball 160 is configured to be displaced from the surface 162 (thus compressing the spring 164) when liquid flows from the reservoir 104 through the inlet flow path 140 and into the pump bulb 120. When the liquid flow from the reservoir 104 is reduced, or more specifically, when the pressure driving the liquid flow from the reservoir 104 is reduced, the spring 164 biases the ball 160 into contact with the surface 162 to seat the ball 160 on the surface 162 and block backflow of the liquid from the bulb 120 back to the reservoir 104. In this manner, the inlet valve 152 is provided as a one-way inlet valve.

The exhaust valve 154 is a one-way valve placed in the pump body 124 to allow liquid to flow out of the pump bulb 120 to the implants 102. The exhaust valve 154 includes a ball 170 that is biased into contact with a surface 172 by a spring 174. The ball 170 is configured to be displaced from the surface 172 (thus compressing the spring 174) when liquid is pushed out of the pump bulb 120 through the exhaust valve 154 and toward the cylinders 102. For example, compressing the pump bulb 120 ejects liquid from the pump bulb 120, which unseats the ball 170 from the surface 172 to allow the liquid to flow past the ball 170 and toward the cylinders 102. The subsequent expansion (or recovery) of the pump bulb 120 again draws liquid from the reservoir 104, past the ball 160, and into the bulb 120 as described above for the inlet valve 152. In this situation, the spring 174 biases the ball 170 into contact with the surface 172 to block backflow of liquid from the cylinders 102 into the pump bulb 120, which allows the pump bulb 120 to again fill with liquid from the reservoir 140. In this manner, the exhaust valve 154 is provided as a one-way exhaust valve.

The deflate valve assembly 150 is not a one-way valve. The stem 182 is movable to allow inflation of the implants 102 in one configuration and to allow deflation of the implants 102 by providing a deflation flow path along the groove 184 when in a second configuration. The deflate valve assembly 150 provides a sealed pathway during inflation, where the sealed pathway prevents deflation during the inflation process. During the deflation process, the deflate valve assembly 150 prevents liquid from flowing back to the pump bulb 120 and prevents flow from entering the implants 102, all of which is described in further detail below.

The sleeve 180 is suitably fabricated from a metal, such as stainless steel, or a plastic, such as polysulfone, or nylon, or polyester. The stem 182 is suitably fabricated by machining or molding, depending upon the material selected, and one suitable choice for the stem 182 is a metal such as stainless steel.

Figure 5:
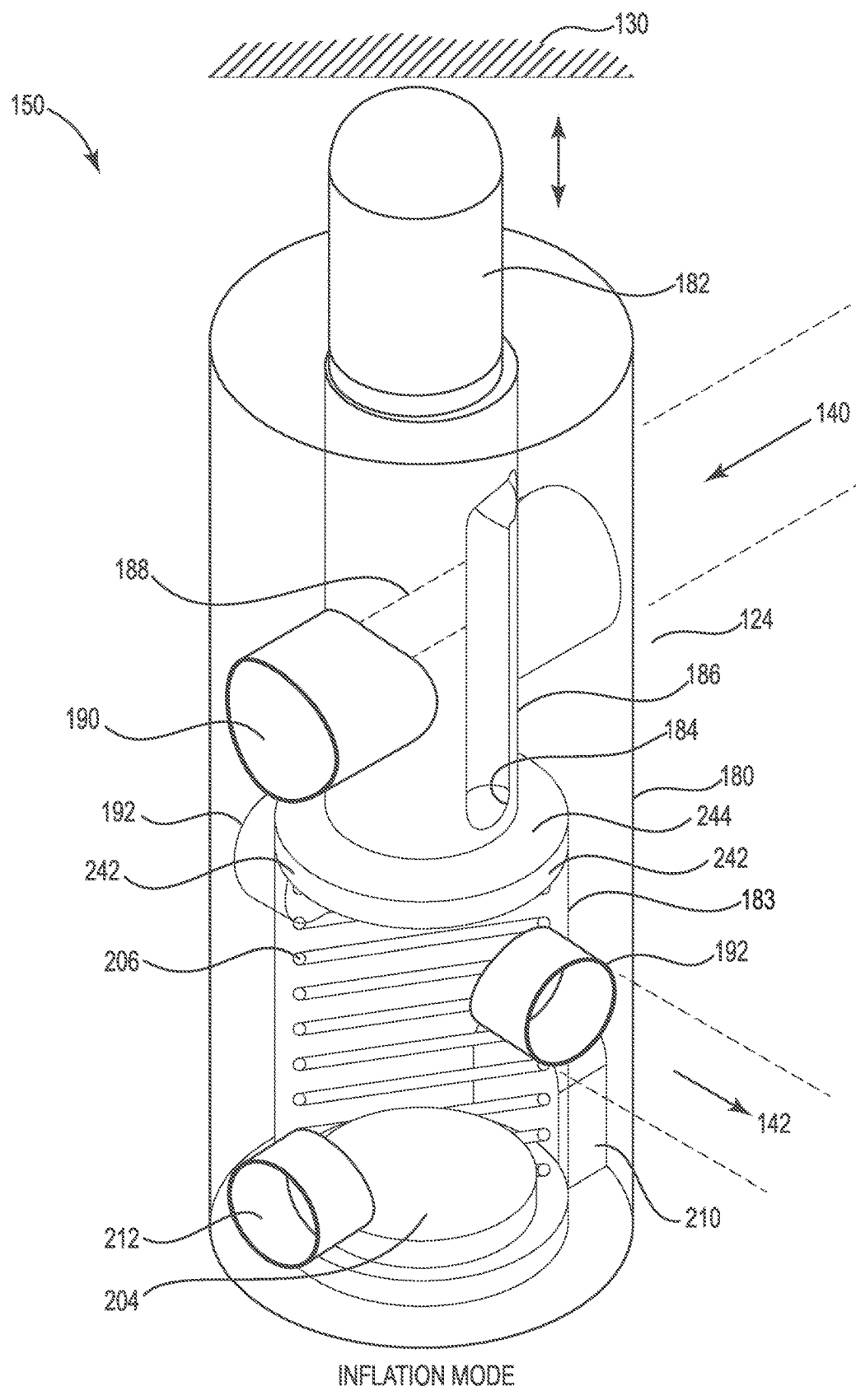
FIG. 5 is a perspective view of one embodiment the deflate valve assembly shown in an inflation mode.
Figure 6:
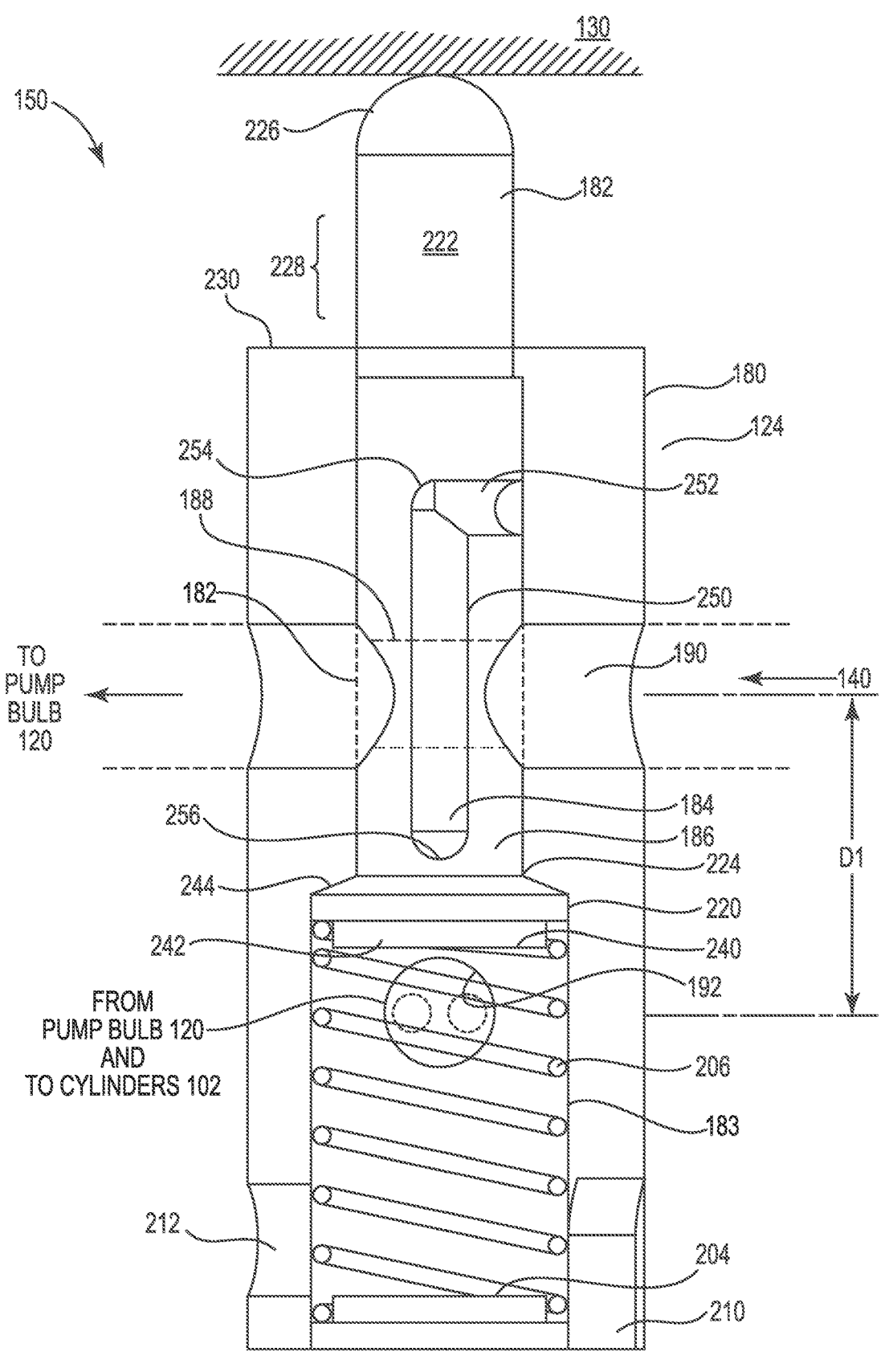
FIG. 6 is a view of the deflate valve assembly in the inflation mode as viewed when looking into the exhaust flow path.

FIG. 5 is a perspective view and FIG. 6 is a right side view of one embodiment of the deflate valve assembly 150 in an inflation mode. The views of FIGS. 5-6 show the sleeve 180 of the deflate valve assembly 150 as it would be when secured inside of a portion of the pump body 124. Consequently, an exhaust lumen 192 is present in the pump body 124 and illustrated projecting through a portion of the pump body 124, where the exhaust lumen 192 is aligned with the outlet flow path (labeled "TO IMPLANTS 102" in FIG. 4).

The deflate valve assembly 150 includes the sleeve 180 sealed inside the pump body 124, the stem 182 that moves longitudinally within and is sealed relative to the channel 183 formed in the sleeve 180, the deflate groove 184 formed in the exterior surface 186 of the stem 182, and the spring 206 that biases the stem 182 within the channel 183 of the sleeve 180.

The stem 182 is provided with an orifice 188 or a groove 188 crossing the stem 182 laterally, and the orifice 188 or groove 188 provides a liquid path through or past the stem 182 that aligns with the inlet flow path 140 when the stem 182 is in the inflation mode (shown in FIGS. 5-6). If the stem 182 is molded from a polymer, then it is preferable for dimensional stability reasons to provide the stem 182 with a groove 188 molded to traverse laterally across a portion of an exterior surface of the stem 182. If the stem 182 is fabricated from a metal, an orifice 188 may be formed through the stem 182 where the amount of material removed from the stem 182 is unlikely to affect dimensional stability of the stem 82. The stem 182 is sealed relative to the channel 183 along the longitudinal sides of the stem 182 and at the location (labeled 244) where a base of the stem 182 meets with the channel 183.

The inflation of the implants 102 operates as described above in FIG. 4 where suction provided by the pump bulb 120 draws liquid out of the reservoir 104, through the inlet flow path 140 and through the orifice 188 of the stem 182, past the inlet valve 152 and into the pump bulb 120. Additional squeezing of the pump bulb 120 pushes the liquid through the exhaust valve 154, under the stem 182, and out of the exhaust flow path 142 into the implants 102.

The deflate valve assembly 150 maintains the stem 182 in the inflation mode within the sleeve 180 during inflation and in a resting or steady state position. In one embodiment, a spring (described below) biases the stem 182 into the inflation mode position during inflation and in the steady state, which allows liquid to flow under the stem 182 during inflation. Consequently, there is no crack force when initiating pumping for liquid flow, and the crack force is eliminated (or the crack force is zero) during the inflation process for the implants 102.

In one embodiment, the stem 182 is metal and may be machined, and stainless steel is one good choice for stem 182. In another embodiment, the stem 182 is molded from a polymer.

For deflation, and with reference to FIG. 5 and FIG. 6, the stem 182 is longitudinally movable within the sleeve 180 (downward relative to FIGS. 5-6) to align the groove 184 with both the inlet flow path 140 and the exhaust flow path 142 to form a deflation flow path in the pump body 124 between the penile implant(s) 102 and the reservoir 104. The deflation flow path is created when the user presses on the deflation pad 130, which displaces the stem 182 downward within the sleeve 180. Displacement of the stem 182 downward aligns the groove 184 with the inlet flow path 140 and the exhaust flow path 142, and the groove 184 provides a pathway that allows the liquid in the inflated (i.e., pressurized) implants 102 to flow (under pressure) along the groove 184 and directly back to the reservoir 104, bypassing the pump bulb 120. The advantage is that the deflation of the implants 102 occurs quickly with one press of the deflation surface 130 of the pump body 124. A return movement of the stem 182 longitudinally within the sleeve 180 (in the upward direction) also operates to selectively move the groove 184 out of alignment with the inlet flow path 140 and the exhaust flow path 142 to return the deflate valve assembly 150 and the pump body 124 back to the inflation mode.

An inlet lumen 190 is formed through the pump body 124 to communicate with the sleeve 180 and the exhaust lumen 192. The inlet lumen 190 is separate from the exhaust lumen 192. The inlet lumen 190 is aligned with the orifice 188 and the inlet flow path 140 when the stem 182 is in the inflation mode. The exhaust lumen 192 is aligned with the exhaust flow path 142 formed in the pump body 124. The exhaust lumen 192 is unobstructed by the stem 182 when the deflate valve assembly 150 is in the inflation mode (FIGS. 5-6). The inlet lumen 190 is not parallel to the exhaust lumen 192, and in one embodiment, the inlet lumen 190 is orthogonal relative to the exhaust lumen 192.

In one embodiment, the stem 182 is biased relative to a base 204 of the sleeve 180 by a spring 206. The spring 206 is metal, and suitable examples of material for the spring 206 include NiTiNOL or steel, such as MP35N steel.

FIG. 6 is a front view of the pump body 124 with the deflate valve assembly 150 in the inflation mode.

After deflation (after the deflation surface 130 has been pressed), the spring 206 pushes the stem 182 longitudinally upward within the sleeve 180 to move the groove 184 out of alignment with the inlet flow path 140 and the exhaust flow path 142, which returns the deflate valve assembly 150 to the inflation mode shown in FIGS. 5-6. The top portion of the base of the stem 182 is sealed within the channel 182 in the inflation mode. The return of the stem 182 to the inflation mode also aligns the orifice 188 formed in the stem 182 with the inlet lumen 190 and the inlet flow path 140, thus the stem 182 is already in position for inflation. Consequently, an initial squeeze of the pump bulb 120 and movement of the liquid through the deflate valve assembly 150 allows inflation of the implants to occur with zero crack force, which is an advantage for those with weakened hands or limited dexterity. The deflate valve assembly 150 positions and maintains the stem 182 within the sleeve 180 in the inflation mode, and thus the crack force is eliminated (or the force is zero) for the entire process of inflation of the implants 102.

Auto-inflation of an inflatable implant can occur when a force is applied to the reservoir (leaning against a tabletop is a typical example where the implanted reservoir becomes pressurized), which results in the liquid in the reservoir possibly flowing to the implants when inflation (erection) is not desired. An anti-auto-inflation valve could be added to the reservoir or to the pump to prevent this undesirable auto-inflation. In any regard, the deflate valve assembly 150 provides a valve that allows inflation (and the initiation of inflation) without a crack force that is associated with other valve assemblies for penile prostheses.

The deflate valve assembly 150 is inserted into the pump body 124. In one embodiment, the deflate valve assembly 150 is inserted into a pump body 124 that is molded in two halves, for example side-by-side, and the deflate valve assembly 150 is placed between the two halves of the pump body 124 before the pump body 124 is welded or glued together into a single piece unit. Another approach is to manufacture a new pump 106 where the deflate valve assembly 150 is molded integrally with the pump body 124. In one embodiment, the deflate valve assembly 150 includes a key 210 that allows the sleeve 180 to be oriented within the pump body 124 in a desired orientation for alignment of the inlet lumen 190 with the orifice 188 and the inlet flow path 140 and alignment of the exhaust lumen 192 with the exhaust flow path 142. An access opening 212 is provided for access to the spring 206.

Figure 7:
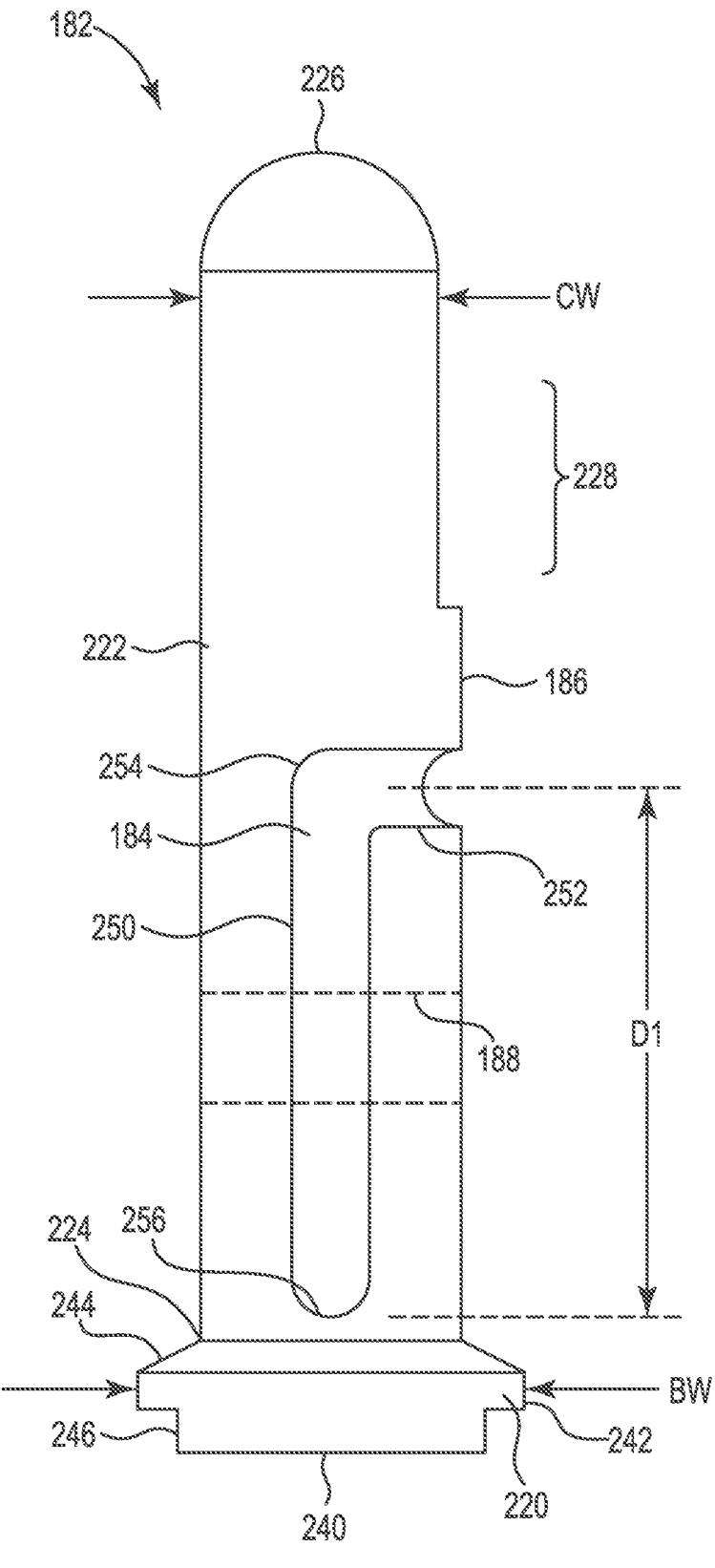
FIG. 7 is a front view of one embodiment of a stem of the deflate valve assembly.
Figure 8:
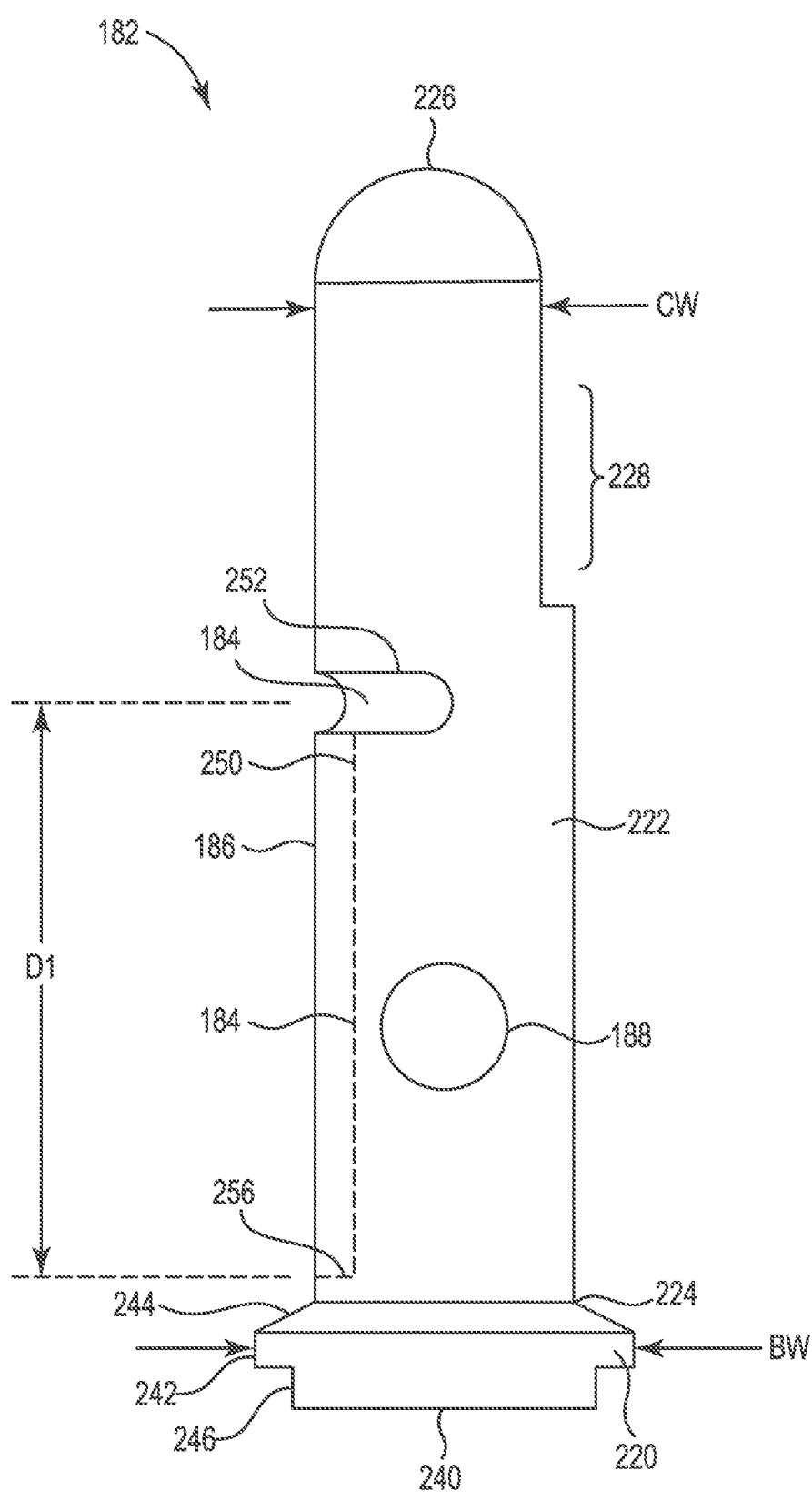
FIG. 8 is a right side view of the stem of the deflate valve assembly.

FIG. 7 is a front view of the stem 182 separated from the sleeve 180 and FIG. 8 is a back view of the stem 182 separated from the sleeve 180.

FIGS. 7-8 are described with additional reference to FIG. 6. The stem 182 includes a base portion 220 and a cylindrical portion 222, with a distal end 224 of the cylindrical portion 222 connected to the base portion 220 and located opposite of a rounded proximal end 226. The rounded proximal end 226 of the cylindrical portion 222 is located adjacent to and under the deflation surface 130 and a proximal portion 228 of the stem 182 is movable through a proximal end 230 of the sleeve when the deflate valve assembly 150 is assembled.

The base portion 220 of the stem 182 includes a distal face 240, a wall 242 orthogonal to and extending away from the distal face 240, and a chamfered surface 244 extending between the wall 242 and the cylindrical portion 222 of the stem 182. A portion 246 of the wall 242 is relieved and sized to receive the spring 206. The chamfered surface 244 is configured to seal relative to the channel 183 (FIG. 6) when the deflate valve assembly 150 in in the inflation mode.

The groove 184 is formed in the exterior surface 186 of the stem 182 and includes a longitudinal segment 250 aligned with a longitudinal axis of the stem 182 and a lateral segment 252 connected to and extending from the longitudinal segment 250. In one embodiment, the lateral segment 252 of the groove 184 extends at a 90-degree angle relative to the longitudinal segment 250. Other orientations and angles of the lateral segment 252 relative to the longitudinal segment 250 are acceptable. For example, with reference to FIGS. 6-7, the groove 184 includes a curved segment 254 connected between the longitudinal segment 250 and the lateral segment 252.

With reference to FIG. 6, the inlet flow path 140 and the inlet lumen 190 are spaced a first distance D1 away from exhaust flow path 142 and the exhaust lumen 192; and with reference to FIG. 8, a distal end 256 of the longitudinal segment 250 of the groove 184 is spaced apart from the lateral segment 252 by the first distance D1.

In one embodiment, best illustrated in the right side view of FIG. 8, the groove 184 is a semicircular groove when viewed in a cross-section orthogonal to a longitudinal axis of the stem.

The base portion 220 has a base width BW that is larger than a width of the cylindrical portion CW of the stem 182, as measured where the chamfered surface 244 meets the wall 242.

The cylindrical portion of the stem 182 extends from the base portion 220, and the cylindrical portion of the stem 182 inserted into a cylindrical recess formed in the sleeve 180 such that an initial movement of the cylindrical portion of the stem 182 within the cylindrical recess in the sleeve 180 is characterized by an absence of a crack force.

The stem 182 is inserted into the sleeve 180. In one embodiment, the proximal portion 228 of the stem 182 is non-concentric relative to the sleeve 180, which is to say that a center of the proximal portion 228 of the stem 182 is not aligned with a center of the sleeve 180. The non-concentric orientation of the proximal portion 228 of the stem 182 relative to the sleeve 180 can be helpful to limit or eliminate axial rotation of the stem 182 within the sleeve 180.

Figure 9:
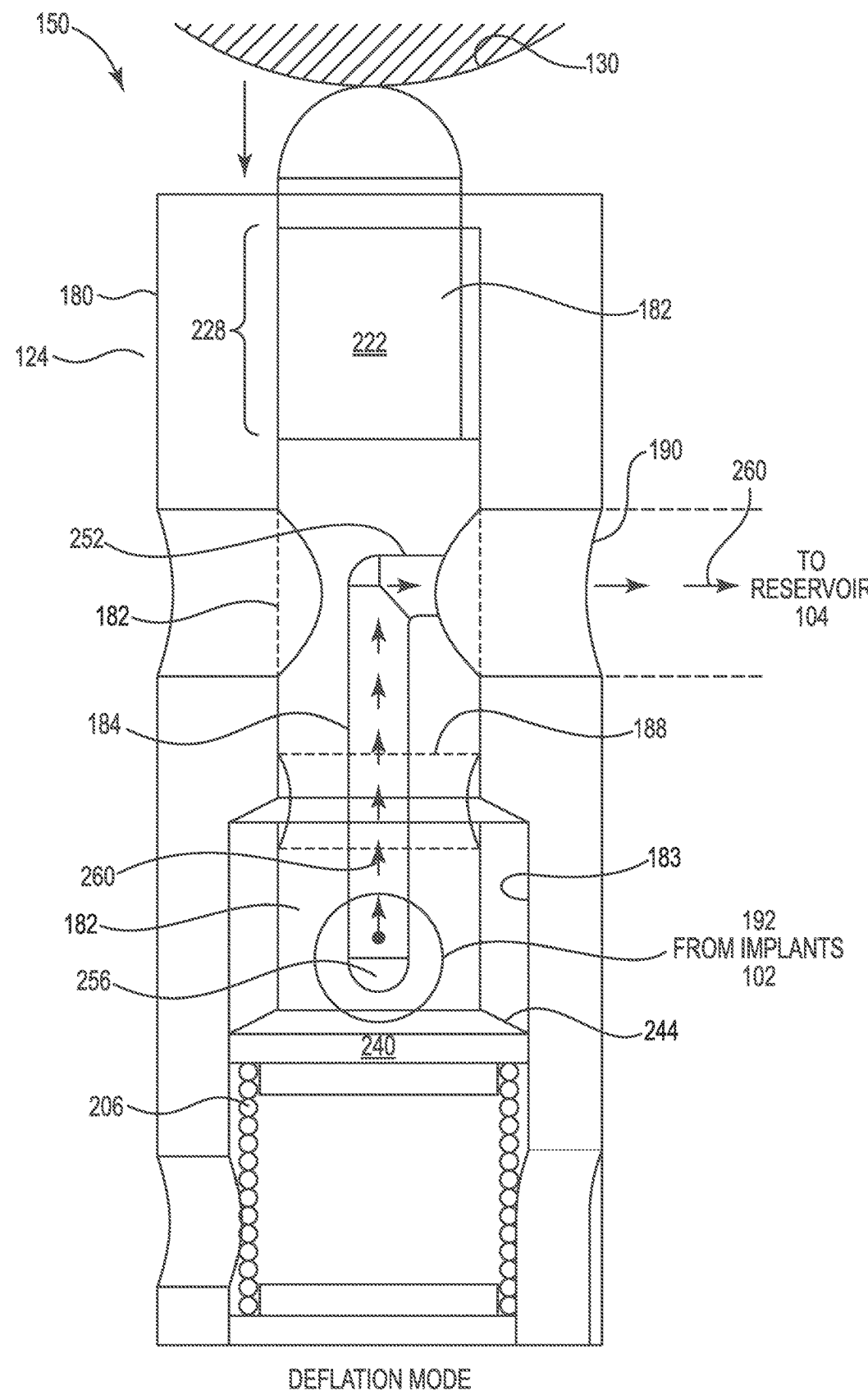
FIG. 9 is a view of the deflate valve assembly in a deflation mode as viewed when looking into the exhaust flow path.

FIG. 9 is a front view of the deflate valve assembly 150 installed within the pump body 124. The deflate valve assembly 150 is in the deflation mode with the stem 182 depressed a distance into the sleeve 180 and the chamfered surface 244 displaced downward from its sealing surface in the channel 183.

In the deflation mode, the cylindrical portion 222 of the stem 182 is pushed into the sleeve 180 by the user pressing on the deflation surface 130. The deflation surface 130 forms a compliant touch pad on an exterior surface of the pump body 124 and pressing the compliant touch pad (surface 130) displaces the surface 130, which displaces the proximal end 226 of the stem 182 longitudinally into the sleeve 180. Note that the proximal portion 228 of the stem 182 has moved longitudinally into the sleeve 180 and the chamfered surface 244 has moved downward and out of sealing engagement with the channel 183. The displacement of the stem 182 aligns the distal end 256 of the longitudinal segment 250 of the groove 184 with the exhaust lumen 192 (and the pair of exhaust tubes 128 of FIG. 3) and positions the lateral segment 252 of the groove 184 into communication with the inlet lumen 190. Since the exhaust lumen 190 is aligned in the exhaust flow path 142, alignment of the distal end 256 of the groove 184 also aligns the groove with the flow path 142 communicating with the implants 102. When the implants 102 are inflated, the liquid in the implants 102 is pressured, and the alignment of the groove 184 between the exhaust lumen 192 and the inlet lumen 190 forms a deflation flow path 260 for the flow of the pressurized liquid from the implants 102, along the groove 184, and directly back to the reservoir 104. After deflation of the implants 102 the spring 206 returns the stem 182 to the inflation position shown in FIGS. 5-6.

Figure 10:
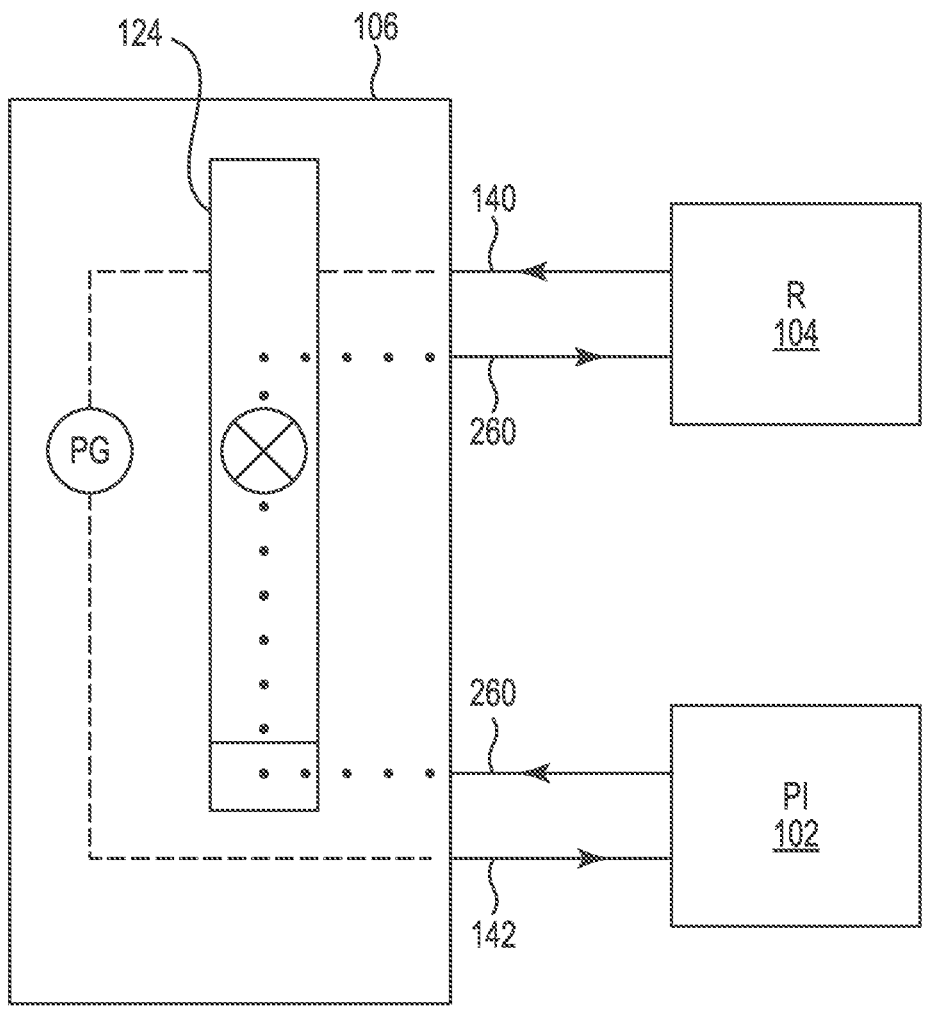
FIG. 10 is a block diagram of one embodiment of a pump communicating with a reservoir and a penile implant of a prosthesis.

FIG. 10 is a block diagram of one embodiment of a pump 106 connected to a reservoir 104 and a penile implant 102 of a prosthesis. The inlet flow path 140 and the exhaust flow path 142 communicate through the pump body 124, with the inlet flow path 140 passing through a pressure generator PG. The pressure generator moves liquid from the reservoir 104 to the implants 102, and in this embodiment is a pump bulb 120. The deflation flow path 260 flows from the implants 102 back to the reservoir 104 through a valve V, bypassing the pressure generator PG.

Figure 11:
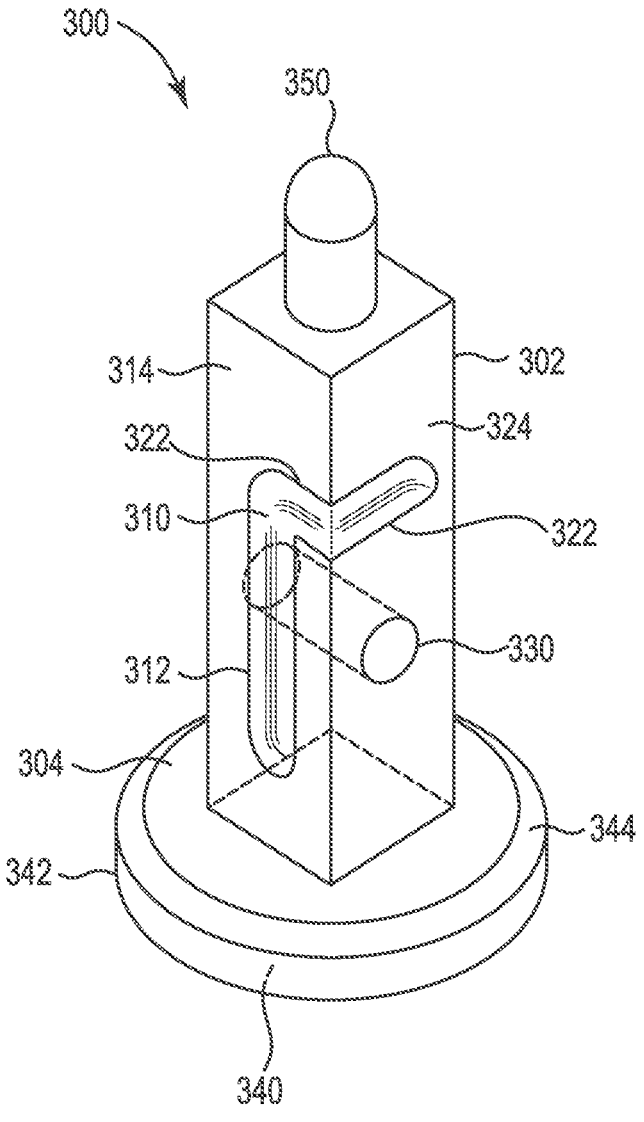
FIG. 11 is a perspective view of one embodiment of a base and a rectangular stem of a deflate valve assembly.

FIG. 11 is a perspective view of one embodiment of a stem 300 for a deflate valve assembly, with the stem 300 having a rectangular projection 302 extending from a base portion 304. The stem 300 is analogous to the stem 182 described above and includes a groove 310 having a longitudinal segment 312 formed in a first face 314 of the rectangular projection 302 and a lateral segment 322 formed along a portion of the first face 314 and along a portion of a second adjacent face 324 of the stem 300. The groove 310 forms a deflation flow path through a pump body in the analogous way that the groove 184 forms the deflation flow path described above.

An orifice 330 is formed through the rectangular projection 302 from the second face 324 to an opposing face of the stem 300. The orifice 330 is configured to be aligned with an inlet flow path formed though the pump body, also as described above for pump body 124.

The base portion 304 includes a distal face 340, a wall 342 extending from the distal face, and a chamfered edge 344. The chamfered edge 344 is adapted to seal relative to the pump body when the stem 300 is assembled in a deflate valve assembly. A proximal end 350 of the rectangular projection 302 is adapted to interact with a deflation surface of the pump body when the stem 300 is assembled in a deflate valve assembly.

The base portion 304 is circular and the projection is rectangular, although other shapes for the base portion 304 are acceptable. The chamfered edge 344 allows the base portion 304 to be sealed to the pump body to prevent leakage of the liquid around the stem 300 during inflation and deflation of the implant.

Figure 12:
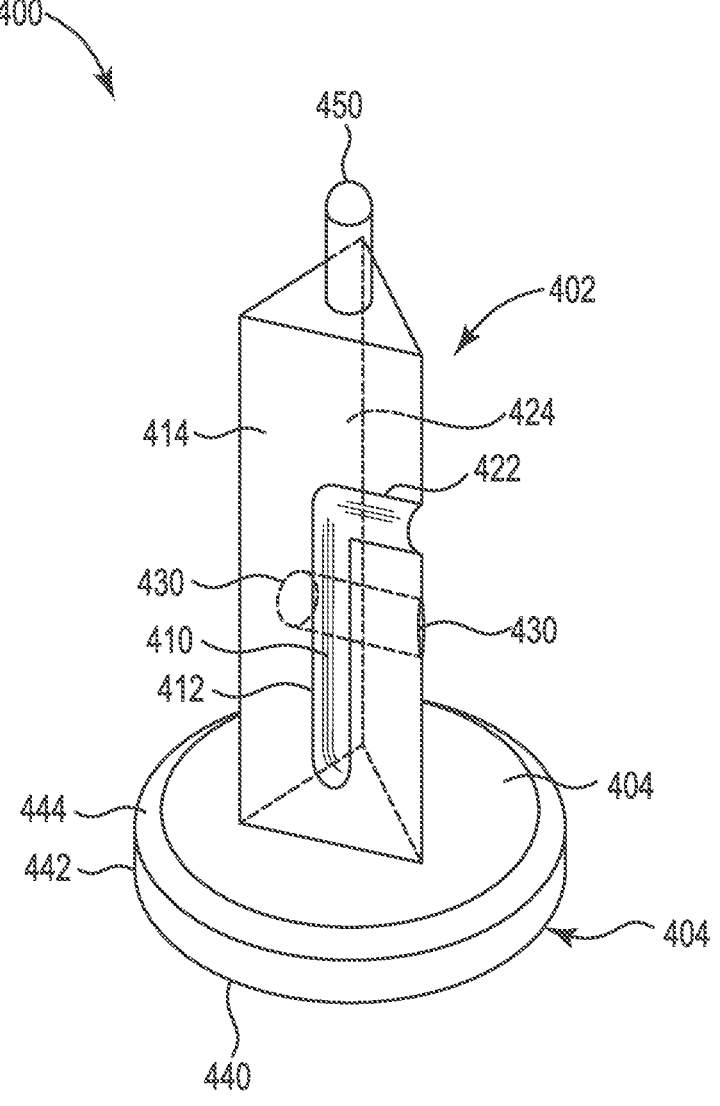
FIG. 12 is a perspective view of one embodiment of a base and a triangular stem of a deflate valve assembly.

FIG. 12 is a perspective view of one embodiment of a stem 400 for a deflate valve assembly, with the stem 400 having a triangular projection 402 extending from a base portion 404. The stem 400 is analogous to the stems 182, 300 described above and includes a groove 410 having a longitudinal segment 412 formed in a first face 414 of the triangular projection 402 and a lateral segment 422 formed along a portion of the first face 414 and along a portion of a second adjacent face 424 of the stem 400. The groove 410 forms a deflation flow path through a pump body in the analogous way that the grooves 184, 310 form the deflation flow path described above.

An orifice 430 is formed through the triangular projection 402 from the second face 424 and through the stem 400. The orifice 430 is configured to be aligned with an inlet flow path formed though the pump body, also as described above for pump body 124.

The base portion 404 includes a distal face 440, a wall 442 extending from the distal face 440, and a chamfered edge 444. The chamfered edge 444 is adapted to seal relative to the pump body when the stem 400 is assembled in a deflate valve assembly. A proximal end 450 of the triangular projection 402 is adapted to interact with a deflation surface of the pump body when the stem 400 is assembled in a deflate valve assembly.

The base portion 304 is circular and the projection is rectangular, although other shapes for the base portion 304 are acceptable. The chamfered edge 344 allows the base portion 304 to be sealed to the pump body to prevent leakage of the liquid around the stem 300 during inflation and deflation of the implant.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein.

What is claimed is:

1. A pump adapted to inflate an implantable penile prosthesis, the pump comprising:

a pump body adapted to be coupled between a penile implant and a reservoir containing a liquid;

an inlet flow path formed in the pump body that is configured to allow the liquid to enter the pump body from the reservoir;

an exhaust flow path formed in the pump body that is configured to allow the liquid to exit the pump body and flow to the penile implant; and a deflate valve assembly comprising a sleeve sealed inside of the pump body and a stem that is movable longitudinally within the sleeve, with a groove formed in an exterior surface of the stem;

wherein the stem is longitudinally movable within the sleeve to align the groove with both the inlet flow path and the exhaust flow path to form a deflation flow path between the penile implant and the reservoir;

wherein the groove includes a longitudinal segment aligned with a longitudinal axis of the stem and a lateral segment connected to and extending from the longitudinal segment.

2. The pump of claim 1, wherein the sleeve includes an inlet lumen formed through the sleeve and an exhaust lumen formed through the sleeve and separate from the inlet lumen, with the inlet lumen aligned with the inlet flow path and the exhaust lumen aligned with the exhaust flow path.

3. The pump of claim 1, wherein a base of the stem is biased relative to a base of the sleeve by a spring.

4. The pump of claim 1, further comprising a pump bulb coupled to the pump body, where the pump bulb is operable to draw the liquid out of the reservoir and eject the liquid to the penile implant.

5. The pump of claim 1, wherein the stem is inserted into the sleeve and the stem is non-concentric relative to the sleeve.

6. The pump of claim 1, wherein the stem comprises a base portion and a cylindrical portion, with a distal end of the cylindrical portion of the stem connected to the base portion and a rounded proximal end of the cylindrical portion of the stem movable through a proximal end of the sleeve.

7. The pump of claim 1, wherein the stem comprises a base portion and a cylindrical portion extending from the base portion, and the base portion comprises a planar distal face, a wall orthogonal to and extending from the planar distal face, and a chamfered surface extending between the wall and the cylindrical portion of the stem.

8. The pump of claim 1, wherein the stem comprises a base portion and a cylindrical portion extending from the base portion, and the base portion has a base width that is larger than a width of the cylindrical portion of the stem.

9. The pump of claim 1, wherein the pump body has a compliant touch pad located on an exterior surface of the pump body, and the compliant touch pad is movable to contact a proximal end of the stem and longitudinally move the stem within the sleeve.

10. The pump of claim 1, wherein the lateral segment of the groove extends at a 90 degree angle relative to the longitudinal segment.

11. The pump of claim 1, wherein the groove comprises a curved segment connected between the longitudinal segment and the lateral segment.

12. The pump of claim 1, wherein the inlet flow path is spaced a first distance away from the exhaust flow path, and a distal end of the longitudinal segment of the groove is spaced apart from the lateral segment by the first distance.

13. The pump of claim 1, wherein the groove is a semicircular groove when viewed in a cross-section orthogonal to a longitudinal axis of the stem.

14. The pump of claim 1, wherein the stem comprises a base portion and a rectangular projection extending from the base portion and the groove includes a longitudinal segment formed in a first face of the rectangular projection of the stem and a lateral segment formed in a second adjacent face of the rectangular projection of the stem.

15. The pump of claim 1, wherein the stem comprises a base portion and a triangular projection extending from the base portion and the groove includes a longitudinal segment formed in a first face of the triangular projection of the stem and a lateral segment formed along a portion of the first face of the triangular projection of the stem and along a portion of a second adjacent face of the triangular projection of the stem.

16. The pump of claim 1, wherein the stem comprises a base portion and a cylindrical portion extending from the base portion, with the cylindrical portion of the stem inserted into a cylindrical recess formed in the sleeve such that an initial movement of the cylindrical portion of the stem within the cylindrical recess in the sleeve is characterized by an absence of a crack force.

17. A pump adapted to inflate an implantable penile prosthesis, the pump comprising:

a pump body adapted to be coupled between a penile implant and a reservoir containing a liquid;

an inlet flow path formed in the pump body that is configured to allow the liquid to enter the pump body from the reservoir;

an exhaust flow path formed in the pump body that is configured to allow the liquid to exit the pump body and flow to the penile implant; and a deflate valve assembly comprising a sleeve sealed inside of the pump body and a stem that is movable longitudinally within the sleeve, with a groove formed in an exterior surface of the stem;

wherein the stem is longitudinally movable within the sleeve to align the groove with both the inlet flow path and the exhaust flow path to form a deflation flow path between the penile implant and the reservoir;

wherein the groove is a semicircular groove when viewed in a cross-section orthogonal to a longitudinal axis of the stem.

* * * * *